United States Patent [19]
Goble et al.

[11] Patent Number: 5,944,715
[45] Date of Patent: Aug. 31, 1999

[54] ELECTROSURGICAL INSTRUMENT

[75] Inventors: Nigel Mark Goble, Cardiff; Colin Charles Owen Goble, Penarth, both of United Kingdom

[73] Assignee: Gyrus Medical Limited, Cardiff, United Kingdom

[21] Appl. No.: 08/756,003

[22] Filed: Nov. 25, 1996

[30] Foreign Application Priority Data

Jun. 29, 1996 [GB] United Kingdom ............... 9612994

[51] Int. Cl.⁶ .................................................. A61B 17/39
[52] U.S. Cl. ............................ 606/41; 606/48; 604/21
[58] Field of Search .............................. 606/32, 35, 38, 606/40, 42, 45–52; 604/21, 22, 114; 607/100–105

[56] References Cited

U.S. PATENT DOCUMENTS

| Re. 33,925 | 5/1992 | Bales et al. . |
|---|---|---|
| 164,184 | 6/1875 | Kidder . |
| 1,366,756 | 1/1921 | Wappler . |
| 1,735,271 | 11/1929 | Groff . |
| 1,814,791 | 7/1931 | Ende . |

(List continued on next page.)

FOREIGN PATENT DOCUMENTS

| 0 013605 | 7/1980 | European Pat. Off. . |
|---|---|---|
| 0 049633 | 4/1982 | European Pat. Off. . |
| 0 067680 | 12/1982 | European Pat. Off. . |
| 0 136855 | 4/1985 | European Pat. Off. . |
| 0 219568 | 12/1985 | European Pat. Off. . |

(List continued on next page.)

OTHER PUBLICATIONS

Cook, Albert M. & John G. Webster, *Therapeutic Medical Devices Application and Design*, Prentice–Hall Inc., New Jersey, 1982, p. 349.

Pearce, John A., *Electrosurgery*, John Wiley & Sons Inc., New York, 1986, pp. 17, 69–75 and 87.

Wyeth, G. A., *Electrosurgical Unit*, pp. 1180–1202.

Everest Medical Technologies, Inc. "Everest Bipolar Laparoscopic Cholecystectomy," Transcript of Lecture by Dr. Olsen, Oct. 7, 1991.

Dobbie, A.K., "The Electrical Aspects of Surgical Diathermy," Biomedical Engineering, May 1969, pp. 206–216.

Valleylab, Excerpts from Valleylab SSE2L Instruction Manual, Valleylab Part No. A 945 110 005 H, Jan. 6, 1983.

Schurr, M. O. et al., "Histologic Effects of Different Technologies for Dissection in Endoscopic Surgery:Nd:YAG Laser, High Frequency and Water–Jet," End. Surg., vol. 2, 1994, pp. 195–201.

(List continued on next page.)

*Primary Examiner*—Michael Peffley
*Attorney, Agent, or Firm*—Nixon & Vanderhye P.C.

[57] ABSTRACT

An electrosurgical instrument, for the treatment of tissue in the presence of an electrically-conductive fluid medium, comprises an instrument shaft, and an electrode assembly at one end of the shaft. The electrode assembly comprises a tissue treatment electrode and a return electrode which is electrically insulated from the tissue treatment electrode by means of an insulation member. The tissue treatment electrode has an exposed end extending laterally through a cut-out provided in the insulation member at the distal end portion of the instrument. The return electrode has a fluid contact surface which overlies the insulation member in the region of the cut-out. The fluid contact surface is spaced from the tissue treatment electrode in such a manner as to define, in use, a conductive fluid path that completes an electrical circuit between the tissue treatment electrode and the return electrode.

35 Claims, 3 Drawing Sheets

U.S. PATENT DOCUMENTS

| | | |
|---|---|---|
| 1,889,609 | 11/1932 | Mutscheller . |
| 1,932,258 | 10/1933 | Wappler . |
| 1,943,543 | 1/1934 | McFadden . |
| 1,952,617 | 3/1934 | Wappler . |
| 1,983,669 | 12/1934 | Kimble . |
| 2,050,904 | 8/1936 | Trice . |
| 2,056,377 | 10/1936 | Wappler . |
| 2,196,171 | 4/1940 | Arnesen . |
| 2,888,298 | 6/1959 | Seiger . |
| 3,035,580 | 5/1962 | Guiorguiev . |
| 3,460,539 | 8/1969 | Anhalt, Sr. . |
| 3,595,239 | 7/1971 | Petersen . |
| 3,601,126 | 8/1971 | Estes . |
| 3,614,414 | 10/1971 | Gores . |
| 3,648,001 | 3/1972 | Anderson et al. . |
| 3,685,518 | 8/1972 | Beurle et al. . |
| 3,707,149 | 12/1972 | Hao et al. . |
| 3,801,766 | 4/1974 | Morrison, Jr. . |
| 3,815,604 | 6/1974 | O'Malley et al. . |
| 3,845,771 | 11/1974 | Vise . |
| 3,847,153 | 11/1974 | Weissman . |
| 3,901,242 | 8/1975 | Storz . |
| 3,902,494 | 9/1975 | Haberlen et al. . |
| 3,903,891 | 9/1975 | Brayshaw . |
| 3,920,021 | 11/1975 | Hiltebrandt . |
| 3,920,022 | 11/1975 | Pastor . |
| 3,923,063 | 12/1975 | Andrews et al. . |
| 3,929,137 | 12/1975 | Gonser et al. . |
| 3,939,839 | 2/1976 | Curtiss . |
| 3,945,375 | 3/1976 | Banko . |
| 3,963,030 | 6/1976 | Newton . |
| 3,964,487 | 6/1976 | Judson . |
| 3,970,088 | 7/1976 | Morrison . |
| 3,974,833 | 8/1976 | Durden, III . |
| 4,011,872 | 3/1977 | Komiya . |
| 4,016,881 | 4/1977 | Rioux et al. . |
| 4,024,467 | 5/1977 | Andrews et al. . |
| 4,033,351 | 7/1977 | Hetzel . |
| 4,040,426 | 8/1977 | Morrison, Jr. . |
| 4,043,342 | 8/1977 | Morrison, Jr. . |
| 4,051,855 | 10/1977 | Schneiderman . |
| 4,060,088 | 11/1977 | Morrison, Jr. et al. . |
| 4,069,827 | 1/1978 | Dominy . |
| 4,074,718 | 2/1978 | Morrison, Jr. . |
| 4,092,986 | 6/1978 | Schneiderman . |
| 4,114,623 | 9/1978 | Meinke et al. . |
| 4,116,198 | 9/1978 | Roos . |
| 4,119,102 | 10/1978 | LeVeen . |
| 4,126,137 | 11/1978 | Archibald . |
| 4,189,685 | 2/1980 | Doss . |
| 4,200,104 | 4/1980 | Harris . |
| 4,202,337 | 5/1980 | Hren et al. . |
| 4,204,549 | 5/1980 | Paglione . |
| 4,210,152 | 7/1980 | Berry . |
| 4,228,800 | 10/1980 | Degler, Jr. et al. . |
| 4,248,231 | 2/1981 | Herczog et al. . |
| 4,271,837 | 6/1981 | Schuler . |
| 4,281,373 | 7/1981 | Mabille . |
| 4,301,802 | 11/1981 | Poler . |
| 4,326,529 | 4/1982 | Doss et al. . |
| 4,346,332 | 8/1982 | Walden . |
| 4,376,263 | 3/1983 | Pittroff et al. . |
| 4,381,007 | 4/1983 | Doss . |
| 4,416,277 | 11/1983 | Newton et al. . |
| 4,418,692 | 12/1983 | Guay . |
| 4,429,698 | 2/1984 | Bentall . |
| 4,448,198 | 5/1984 | Turner . |
| 4,474,179 | 10/1984 | Koch . |
| 4,476,862 | 10/1984 | Pao . |
| 4,492,231 | 1/1985 | Auth . |
| 4,494,541 | 1/1985 | Archibald . |
| 4,512,338 | 4/1985 | Balko et al. . |
| 4,524,770 | 6/1985 | Orandi . |
| 4,532,924 | 8/1985 | Auth et al. . |
| 4,534,347 | 8/1985 | Taylor . |
| 4,548,207 | 10/1985 | Reimels . |
| 4,559,943 | 12/1985 | Bowers . |
| 4,559,951 | 12/1985 | Dahl et al. . |
| 4,562,838 | 1/1986 | Walker . |
| 4,565,200 | 1/1986 | Cosman . |
| 4,567,890 | 2/1986 | Ohta et al. . |
| 4,580,557 | 4/1986 | Hertzmann . |
| 4,590,934 | 5/1986 | Malis et al. . |
| 4,593,691 | 6/1986 | Lindstrom et al. . |
| 4,617,927 | 10/1986 | Manes . |
| 4,657,015 | 4/1987 | Irnich . |
| 4,658,819 | 4/1987 | Harris et al. . |
| 4,658,820 | 4/1987 | Klicek . |
| 4,669,468 | 6/1987 | Cartmell et al. . |
| 4,674,499 | 6/1987 | Pao . |
| 4,681,122 | 7/1987 | Winters et al. . |
| 4,682,596 | 7/1987 | Bales et al. . |
| 4,688,569 | 8/1987 | Rabinowitz . |
| 4,696,668 | 9/1987 | Wilcox . |
| 4,706,667 | 11/1987 | Roos . |
| 4,709,698 | 12/1987 | Johnston et al. . |
| 4,712,544 | 12/1987 | Ensslin . |
| 4,727,874 | 3/1988 | Bowers et al. . |
| 4,735,201 | 4/1988 | O'Reilly . |
| 4,769,005 | 9/1988 | Ginsburg et al. . |
| 4,781,175 | 11/1988 | McGreevy et al. . |
| 4,799,480 | 1/1989 | Abraham et al. . |
| 4,800,899 | 1/1989 | Elliott . |
| 4,802,476 | 2/1989 | Noerenberg et al. . |
| 4,805,616 | 2/1989 | Pao . |
| 4,813,429 | 3/1989 | Eshel et al. . |
| 4,820,298 | 4/1989 | Leveen et al. . |
| 4,823,791 | 4/1989 | D'Amelio et al. . |
| 4,827,927 | 5/1989 | Newton ................................. 606/39 |
| 4,832,048 | 5/1989 | Cohen . |
| 4,850,353 | 7/1989 | Stasz et al. . |
| 4,860,744 | 8/1989 | Johnson et al. . |
| 4,878,493 | 11/1989 | Pasternak et al. . |
| 4,886,074 | 12/1989 | Bisping . |
| 4,919,129 | 4/1990 | Weber, Jr. et al. . |
| 4,920,978 | 5/1990 | Colvin . |
| 4,931,047 | 6/1990 | Broadwin et al. . |
| 4,936,281 | 6/1990 | Stasz . |
| 4,936,301 | 6/1990 | Rexroth et al. . |
| 4,936,310 | 6/1990 | Engstrom et al. . |
| 4,936,842 | 6/1990 | D'Amelio et al. . |
| 4,943,290 | 7/1990 | Rexroth et al. . |
| 4,950,267 | 8/1990 | Ishihara et al. . |
| 4,955,377 | 9/1990 | Lennox et al. . |
| 4,966,597 | 10/1990 | Cosman . |
| 4,967,765 | 11/1990 | Turner et al. . |
| 4,969,885 | 11/1990 | Farin . |
| 4,976,711 | 12/1990 | Parins et al. . |
| 4,994,069 | 2/1991 | Ritchart et al. . |
| 4,998,933 | 3/1991 | Eggers et al. . |
| 5,007,908 | 4/1991 | Rydell . |
| 5,009,656 | 4/1991 | Reimels . |
| 5,013,312 | 5/1991 | Parins et al. ................................. 606/39 |
| 5,019,076 | 5/1991 | Yamanashi et al. . |
| 5,035,696 | 7/1991 | Rydell ................................. 606/47 |
| 5,037,379 | 8/1991 | Clayman et al. . |
| 5,047,026 | 9/1991 | Rydell . |
| 5,047,027 | 9/1991 | Rydell . |
| 5,057,107 | 10/1991 | Parins et al. ................................. 606/48 |
| 5,062,031 | 10/1991 | Flachenecker et al. . |
| 5,071,418 | 12/1991 | Rosenbaum . |
| 5,080,660 | 1/1992 | Buelna ................................. 606/45 |

| | | | | | |
|---|---|---|---|---|---|
| 5,083,565 | 1/1992 | Parins . | 5,422,567 | 6/1995 | Matsunaga . |
| 5,085,659 | 2/1992 | Rydell . | 5,423,808 | 6/1995 | Edwards et al. . |
| 5,088,997 | 2/1992 | Delahuerga et al. . | 5,423,809 | 6/1995 | Klicek . |
| 5,098,431 | 3/1992 | Rydell . | 5,423,810 | 6/1995 | Goble et al. . |
| 5,099,840 | 3/1992 | Goble et al. . | 5,423,811 | 6/1995 | Imran et al. . |
| 5,108,391 | 4/1992 | Flachenecker et al. .......... 606/38 | 5,431,649 | 7/1995 | Mulier et al. . |
| 5,108,407 | 4/1992 | Geremia et al. . | 5,437,662 | 8/1995 | Nardella . |
| 5,117,978 | 6/1992 | Blumenfeld et al. . | 5,438,302 | 8/1995 | Goble . |
| 5,122,138 | 6/1992 | Manwaring . | 5,441,499 | 8/1995 | Fritzsch . |
| 5,133,365 | 7/1992 | Heil, Jr. et al. . | 5,443,470 | 8/1995 | Stern et al. . |
| 5,158,561 | 10/1992 | Rydell et al. .................. 606/39 | 5,454,809 | 10/1995 | Janssen . |
| 5,167,658 | 12/1992 | Ensslin . | 5,462,521 | 10/1995 | Brucker et al. . |
| 5,167,659 | 12/1992 | Ohtomo et al. . | 5,472,441 | 12/1995 | Edwards et al. . |
| 5,171,255 | 12/1992 | Rydell . | 5,472,443 | 12/1995 | Cordis et al. . |
| 5,171,311 | 12/1992 | Rydell et al. . | 5,480,397 | 1/1996 | Eggers et al. . |
| 5,178,620 | 1/1993 | Eggers et al. . | 5,480,398 | 1/1996 | Eggers et al. . |
| 5,190,517 | 3/1993 | Zieve et al. . | 5,496,312 | 3/1996 | Klicek . |
| 5,195,959 | 3/1993 | Smith . | 5,496,314 | 3/1996 | Eggers . |
| 5,196,007 | 3/1993 | Ellman et al. . | 5,505,728 | 4/1996 | Ellman et al. . |
| 5,197,963 | 3/1993 | Parins . | 5,505,730 | 4/1996 | Edwards . |
| 5,201,743 | 4/1993 | Haber et al. . | 5,507,743 | 4/1996 | Edwards et al. . |
| 5,207,675 | 5/1993 | Canady . | 5,514,129 | 5/1996 | Smith . |
| 5,217,457 | 6/1993 | Delahuerga et al. . | 5,514,130 | 5/1996 | Baker . |
| 5,217,458 | 6/1993 | Parins . | 5,514,131 | 5/1996 | Edwards et al. . |
| 5,217,459 | 6/1993 | Kamerling . | 5,520,684 | 5/1996 | Imran . |
| 5,221,281 | 6/1993 | Klicek . | 5,520,685 | 5/1996 | Wojciechowicz . |
| 5,244,462 | 9/1993 | Delahuerga et al. . | 5,522,815 | 6/1996 | Durgin, Jr. et al. . |
| 5,249,585 | 10/1993 | Turner et al. . | 5,531,744 | 7/1996 | Nardella et al. . |
| 5,250,047 | 10/1993 | Rydell . | 5,536,267 | 7/1996 | Edwards et al. . |
| 5,258,006 | 11/1993 | Rydell et al. . | 5,540,680 | 7/1996 | Guglielmi et al. . |
| 5,259,395 | 11/1993 | Li . | 5,540,681 | 7/1996 | Strul et al. . |
| 5,261,906 | 11/1993 | Pennino et al. . | 5,540,682 | 7/1996 | Gardner et al. . |
| 5,267,994 | 12/1993 | Gentelia et al. . | 5,540,683 | 7/1996 | Ichikawa et al. . |
| 5,267,997 | 12/1993 | Farin et al. . | 5,540,684 | 7/1996 | Hassler, Jr. . |
| 5,277,201 | 1/1994 | Stern . | 5,540,685 | 7/1996 | Parins et al. . |
| 5,277,696 | 1/1994 | Hagen . | 5,542,916 | 8/1996 | Hirsch et al. . |
| 5,281,213 | 1/1994 | Milder et al. . | 5,542,945 | 8/1996 | Fritzsch . |
| 5,281,216 | 1/1994 | Klicek . | 5,545,161 | 8/1996 | Imran . |
| 5,282,799 | 2/1994 | Rydell . | 5,545,193 | 8/1996 | Fleischman et al. . |
| 5,282,845 | 2/1994 | Bush et al. . | 5,549,605 | 8/1996 | Hahnen . |
| 5,290,282 | 3/1994 | Casscells . | 5,554,172 | 9/1996 | Horner et al. . |
| 5,290,283 | 3/1994 | Suda . | 5,555,618 | 9/1996 | Winkler . |
| 5,300,039 | 4/1994 | Hunsberger et al. . | 5,556,396 | 9/1996 | Cohen et al. . |
| 5,300,068 | 4/1994 | Rosar et al. . | 5,556,397 | 9/1996 | Long et al. . |
| 5,300,070 | 4/1994 | Gentelia et al. . | 5,558,671 | 9/1996 | Yates . |
| 5,304,214 | 4/1994 | DeFord et al. . | 5,562,720 | 10/1996 | Stern et al. . |
| 5,306,238 | 4/1994 | Fleenor . | 5,569,164 | 10/1996 | Lurz . |
| 5,318,563 | 6/1994 | Malis et al. . | 5,569,242 | 10/1996 | Lax et al. . |
| 5,320,627 | 6/1994 | Sorensen et al. . | 5,569,244 | 10/1996 | Hahnen . |
| 5,330,470 | 7/1994 | Hagen . | 5,569,245 | 10/1996 | Guglielmi et al. . |
| 5,330,471 | 7/1994 | Eggers . | 5,571,100 | 11/1996 | Goble et al. . |
| 5,334,193 | 8/1994 | Nardella . | 5,575,789 | 11/1996 | Bell et al. . |
| 5,334,198 | 8/1994 | Hart et al. . | 5,578,007 | 11/1996 | Imran . |
| 5,336,222 | 8/1994 | Durgin, Jr. et al. . | 5,582,609 | 12/1996 | Swanson et al. . |
| 5,342,357 | 8/1994 | Nardella . | 5,582,610 | 12/1996 | Grossi et al. . |
| 5,342,391 | 8/1994 | Foshee et al. . | 5,584,830 | 12/1996 | Ladd et al. . |
| 5,344,428 | 9/1994 | Griffiths . | 5,591,141 | 1/1997 | Nettekoven . |
| 5,352,222 | 10/1994 | Rydell . | 5,599,344 | 2/1997 | Paterson . |
| 5,354,296 | 10/1994 | Turkel . | 5,599,345 | 2/1997 | Edwards et al. . |
| 5,366,443 | 11/1994 | Eggers et al. . | 5,599,346 | 2/1997 | Edwards et al. . |
| 5,370,645 | 12/1994 | Klicek et al. . | 5,599,347 | 2/1997 | Hart et al. . |
| 5,370,675 | 12/1994 | Edwards et al. . | 5,599,348 | 2/1997 | Gentelia et al. . |
| 5,372,596 | 12/1994 | Klicek et al. . | 5,599,349 | 2/1997 | D'Amelio . |
| 5,382,247 | 1/1995 | Cimino et al. . | 5,603,711 | 2/1997 | Parins et al. . |
| 5,383,874 | 1/1995 | Jackson et al. . | 5,603,712 | 2/1997 | Koranda et al. . |
| 5,383,876 | 1/1995 | Nardella . | 5,607,422 | 3/1997 | Smeets et al. . |
| 5,383,917 | 1/1995 | Desai et al. . | 5,609,151 | 3/1997 | Mulier et al. . |
| 5,383,923 | 1/1995 | Webster, Jr. . | 5,609,573 | 3/1997 | Sandock . |
| 5,395,363 | 3/1995 | Billings et al. . | 5,611,798 | 3/1997 | Eggers . |
| 5,395,368 | 3/1995 | Ellman et al. . | 5,620,481 | 4/1997 | Desai et al. . |
| 5,403,311 | 4/1995 | Abele et al. . | 5,624,439 | 4/1997 | Edwards et al. . |
| 5,419,767 | 5/1995 | Eggers et al. . | 5,626,560 | 5/1997 | Soring . |

| | | |
|---|---|---|
| 5,626,575 | 5/1997 | Crenner . |
| 5,626,576 | 5/1997 | Janssen . |
| 5,626,578 | 5/1997 | Tihon . |
| 5,628,745 | 5/1997 | Bek . |
| 5,628,771 | 5/1997 | Mizukawa et al. . |
| 5,630,426 | 5/1997 | Eggers et al. . |
| 5,633,578 | 5/1997 | Eggers et al. . |
| 5,634,924 | 6/1997 | Turkel et al. . |
| 5,672,174 | 9/1997 | Gough et al. . |
| 5,683,366 | 11/1997 | Eggers et al. . |
| 5,693,045 | 12/1997 | Eggers . |
| 5,697,281 | 12/1997 | Eggers et al. . |
| 5,697,536 | 12/1997 | Eggers et al. . |
| 5,697,882 | 12/1997 | Eggers et al. . |
| 5,697,909 | 12/1997 | Eggers et al. . |
| 5,700,262 | 12/1997 | Acosta et al. . |
| 5,766,153 | 6/1998 | Eggers et al. . |
| 5,810,764 | 9/1998 | Eggers et al. . |
| 5,843,019 | 12/1998 | Eggers et al. ............................... 604/22 |
| 5,860,951 | 1/1999 | Eggers et al. ............................... 604/49 |
| 5,871,469 | 2/1999 | Eggers et al. ........................... 604/114 |
| 5,873,855 | 2/1999 | Eggers et al. . |

FOREIGN PATENT DOCUMENTS

| | | |
|---|---|---|
| 0 280798 | 9/1988 | European Pat. Off. . |
| 0 310431 | 4/1989 | European Pat. Off. . |
| 0 316469 | 5/1989 | European Pat. Off. . |
| 0 325456 | 7/1989 | European Pat. Off. . |
| 0 332308 | 9/1989 | European Pat. Off. . |
| 0 205 851 | 2/1990 | European Pat. Off. . |
| 0 373670 | 6/1990 | European Pat. Off. . |
| 0 392837 | 10/1990 | European Pat. Off. . |
| 0 407057 | 1/1991 | European Pat. Off. . |
| 0 412426 | 2/1991 | European Pat. Off. . |
| 0 437377 | 7/1991 | European Pat. Off. . |
| 0 448798 | 10/1991 | European Pat. Off. . |
| 0 499491 | 8/1992 | European Pat. Off. . |
| 0 507622 | 10/1992 | European Pat. Off. . |
| 0 509670 | 10/1992 | European Pat. Off. . |
| 0 517243 | 12/1992 | European Pat. Off. . |
| 0 518230 | 12/1992 | European Pat. Off. . |
| 0 530400 | 3/1993 | European Pat. Off. . |
| 0 536440 | 4/1993 | European Pat. Off. . |
| 0 558316 | 9/1993 | European Pat. Off. . |
| 0 558318 | 9/1993 | European Pat. Off. . |
| 0 647435 | 4/1995 | European Pat. Off. . |
| 0 653192 | 5/1995 | European Pat. Off. . |
| 0 667680 | 8/1995 | European Pat. Off. . |
| 0 674909 | 10/1995 | European Pat. Off. . |
| 0 684015 | 11/1995 | European Pat. Off. . |
| 0 688536 | 12/1995 | European Pat. Off. . |
| 0 692224 | 1/1996 | European Pat. Off. . |
| 0 694290 | 1/1996 | European Pat. Off. . |
| 0 697199 | 2/1996 | European Pat. Off. . |
| 0 709065 | 5/1996 | European Pat. Off. . |
| 0 714635 | 6/1996 | European Pat. Off. . |
| 0 717967 | 6/1996 | European Pat. Off. . |
| 0 732080 | 9/1996 | European Pat. Off. . |
| 0 733345 | 9/1996 | European Pat. Off. . |
| 0 737447 | 10/1996 | European Pat. Off. . |
| 0 740926 | 11/1996 | European Pat. Off. . |
| 57862 | 9/1953 | France . |
| 1215305 | 4/1960 | France . |
| 1454773 | 10/1966 | France . |
| 2313949 | 1/1977 | France . |
| 2443829 | 7/1980 | France . |
| 2501034 | 9/1982 | France . |
| 651428 | 9/1937 | Germany . |
| 1007960 | 5/1957 | Germany . |
| 2222820 | 11/1973 | Germany . |
| 2457900 | 5/1976 | Germany . |
| 2930982 | 2/1981 | Germany . |
| 3209444 | 10/1982 | Germany . |
| 3215832 | 11/1982 | Germany . |
| 3119735 | 1/1983 | Germany . |
| 3245570 | 6/1984 | Germany . |
| 222207 | 5/1985 | Germany . |
| 3423356 | 1/1986 | Germany . |
| 3427517 | 1/1986 | Germany . |
| 3511107 | 10/1986 | Germany . |
| 3623688 | 1/1987 | Germany . |
| 3530335 | 3/1987 | Germany . |
| 3707820 | 9/1987 | Germany . |
| 3622337 C2 | 1/1988 | Germany . |
| 3642077 C2 | 6/1988 | Germany . |
| 3708801 C2 | 9/1988 | Germany . |
| 3824913 | 2/1990 | Germany . |
| 3838840 C2 | 5/1990 | Germany . |
| 3930451 | 3/1991 | Germany . |
| 4108269 C2 | 6/1992 | Germany . |
| 4103972 C2 | 8/1992 | Germany . |
| 4126608 | 2/1993 | Germany . |
| 4139029 C2 | 6/1993 | Germany . |
| 4217999 A1 | 12/1993 | Germany . |
| 4237321 A1 | 5/1994 | Germany . |
| 4323585 | 1/1995 | Germany . |
| 4339049 | 5/1995 | Germany . |
| 4425015 | 1/1996 | Germany . |
| 19530004 | 3/1996 | Germany . |
| 4429478 | 3/1996 | Germany . |
| 19510185 | 10/1996 | Germany . |
| 19512640 C2 | 10/1996 | Germany . |
| 19514552 | 10/1996 | Germany . |
| 19514553 C1 | 10/1996 | Germany . |
| 62-211060 | 9/1987 | Japan . |
| 644491 | 1/1979 | Russian Federation . |
| 243478 | 7/1946 | Switzerland . |
| 1361497 | 7/1974 | United Kingdom . |
| 2037167 | 7/1980 | United Kingdom . |
| 1583397 | 1/1981 | United Kingdom . |
| 2133290 | 7/1984 | United Kingdom . |
| 2145932 | 4/1985 | United Kingdom . |
| 2161081 | 1/1986 | United Kingdom . |
| 2164473 | 3/1986 | United Kingdom . |
| 2177309 | 1/1987 | United Kingdom . |
| 2179861 | 3/1987 | United Kingdom . |
| 2213381 | 8/1989 | United Kingdom . |
| 2214430 | 9/1989 | United Kingdom . |
| WO 81/03271 | 11/1981 | WIPO . |
| WO 82/00084 | 1/1982 | WIPO . |
| WO 82/02488 | 8/1982 | WIPO . |
| WO 84/03829 | 10/1984 | WIPO . |
| WO 88/01851 | 3/1988 | WIPO . |
| WO 90/03152 | 4/1990 | WIPO . |
| WO 93/08756 | 5/1993 | WIPO . |
| WO 93/13718 | 7/1993 | WIPO . |
| WO 93/13816 | 7/1993 | WIPO . |
| WO 93/16650 | 9/1993 | WIPO . |
| WO 93/02877 | 10/1993 | WIPO . |
| WO 93/19682 | 10/1993 | WIPO . |
| WO 93/20747 | 10/1993 | WIPO . |
| wO 93/19681 | 10/1993 | WIPO . |
| WO 94/04220 | 3/1994 | WIPO . |
| WO 94/06510 | 3/1994 | WIPO . |
| WO 94/10921 | 5/1994 | WIPO . |
| WO 94/10924 | 5/1994 | WIPO . |
| WO 94/10925 | 5/1994 | WIPO . |
| WO 94/23659 | 10/1994 | WIPO . |
| wo 94/26228 | 11/1994 | WIPO . |
| WO 94/28809 | 12/1994 | WIPO . |
| WO 95/02369 | 1/1995 | WIPO . |
| WO 95/05781 | 3/1995 | WIPO . |
| WO 95/09576 | 4/1995 | WIPO . |
| WO 95/09577 | 4/1995 | WIPO . |

| | | |
|---|---|---|
| WO 95/10320 | 4/1995 | WIPO . |
| WO 95/10321 | 4/1995 | WIPO . |
| WO 95/17855 | 7/1995 | WIPO . |
| WO 95/18575 | 7/1995 | WIPO . |
| WO 95/19733 | 7/1995 | WIPO . |
| WO 95/20360 | 8/1995 | WIPO . |
| WO 95/23558 | 9/1995 | WIPO . |
| WO 95/24160 | 9/1995 | WIPO . |
| WO 95/25472 | 9/1995 | WIPO . |
| WO 95/26686 | 10/1995 | WIPO . |
| WO 95/30377 | 11/1995 | WIPO . |
| WO 95/31144 | 11/1995 | WIPO . |
| WO 96/00036 | 1/1996 | WIPO . |
| WO 96/00040 | 1/1996 | WIPO . |
| WO 96/00042 | 1/1996 | WIPO . |
| WO 96/00043 | 1/1996 | WIPO . |
| WO 96/00528 | 1/1996 | WIPO . |
| WO 96/04859 | 2/1996 | WIPO . |
| WO 96/07360 | 3/1996 | WIPO . |
| WO 96/09010 | 3/1996 | WIPO . |
| WO 96/10367 | 4/1996 | WIPO . |
| WO 96/14020 | 5/1996 | WIPO . |
| WO 96/14021 | 5/1996 | WIPO . |
| WO 96/18349 | 6/1996 | WIPO . |
| WO 96/19152 | 6/1996 | WIPO . |
| WO 96/23448 | 8/1996 | WIPO . |
| WO 96/23449 | 8/1996 | WIPO . |
| WO 96/24296 | 8/1996 | WIPO . |
| WO 96/24301 | 8/1996 | WIPO . |
| WO 96/27337 | 9/1996 | WIPO . |
| WO 96/29946 | 10/1996 | WIPO . |
| WO 96/32897 | 10/1996 | WIPO . |
| WO 96/34567 | 11/1996 | WIPO . |
| WO 96/34569 | 11/1996 | WIPO . |
| WO 96/34570 | 11/1996 | WIPO . |
| WO 96/34571 | 11/1996 | WIPO . |

OTHER PUBLICATIONS

Newman, Laura, "Could Twist on TURP Knock Lasers Out," Urology Times, vol. 3, No. 3, Mar. 1995, p. 21.

ArthroCare Corporation, "The Arthrocare Arthroscopic System," 1995.

Tucker, R.D. et al., "In Vivo Effect of 5 French Bipolar and Monopolar Electro–Surgical Probes on Porcine Bladder," Urological Research, Springer–Verlag 1990, 18:291–294.

Kramolowsky, Eugene V. et al., "The Urological Application of Electrosurgery," The Journal of Urology, vol. 146, Sep. 1991, pp. 669–674.

Tucker, Robert D. et al., "A Comparison of Urologic Application of Bipolar Versus Monopolar Five French Electrosurgical Probes," The Journal of Urology, vol. 141, Mar. 1989, pp. 662–665.

Kramolowsky, Eugene V. et al., "Use of 5F Bipolar Electrosurgical Probe in Endoscopic Urological Procedures," The Journal of Urology, vol. 143, Feb. 1990, pp. 275–277.

Tucker, Robert et al., A Bipolar Electrosurgical TURP Loop, Abstract of Paper P14–11, $7^{th}$ World Congress on Endourology and ESWL, Nov. 27–30, Kyoto, Japan, 1989, p. 248.

Ramsay, J.W. A. et al., "A Comparison of Bipolar and Monopolar Diathermy Probes in Experimental Animals," Urological Research, Springer–Verlag 1985, 13:99–102.

German Article w/Translation: Elsasser, E. and Roos, E., "Concerning an Instrument for Transurethral Resection without Leakage of Current," Medizinal–Marks/Acta Medicotechnica, vol. 24, No. 4, 1976, pp. 129–134.

Nardella, Paul C., "Radio Frequency Energy and Impedance Feedback," SPIE, vol. 1068, Catheter–Based Sensing & Imaging Technology, 1989, pp. 42–48.

Honig, William M., "The Mechanism of Cutting in Electrosurgery," IEEE Transactions on Biomedical Engineering, Jan. 1975, pp. 58–65.

Barry, Kevin J. et al., "The Effect of Radiofrequency–Generated Thermal Energy on the Mechanical and Histologic Characteristics of the Arterial Wall In Vivo: Implications for Radiofrequency Angioplasty," American Heart Journal, vol. 117, No. 2, Feb. 1989, pp. 332–341.

Slager, Cornelis J. et al., "Vaporization of Atherosclerotic Plaques by Spark Erosion," Journal of American College of Cardiology, 1985, pp. 1382–1386.

Lee, Benjamin I. et al., "Thermal Compression and Molding of Atherosclerotic Vascular Tissue with Use of Radiofrequency Energy: Implications for Radiofrequency Balloon Angioplasty," Journal of American College Cardiology, vol. 13, No. 5, Apr. 1989, pp. 1167–1175.

Piercey, J.R.A. et al., "Electrosurgical Treatment of Experimental Bleeding Canine Gastric Ulcers," Gastroenterology, vol. 74, No. 3, 1978, pp. 527–534.

Protell, Robert L. et al., "Computer–Assisted Electrocoagulation: Bipolar vs. Monopolar in the Treatment of Experimental Canine Gastric Ulcer Bleeding," Gastroenterology, vol. 80, No. 3, 1981, pp. 451–455.

Johnston, James H. et al., "Experimental Comparison of Endoscopic Yttrium–Aluminum–Garnet Laser, Electrosurgery, and Heater Probe for Canine Gut Arterial Coagulation," Gastroenterology, vol. 92, No. 5, May 1987, pp. 1101–1108.

Dennis, M.B. et al., "Evaluation of Electrofulguration in Control of Bleeding of Experimental Gastric Ulcers," Digestive Diseases and Sciences, vol. 24, No. 11, Nov. 1979, pp. 845–848.

Silverstein, Fred E. et al., "Endoscopic Hemostasis Using Laser Photocoagulation and Electrocoagulation," Digestive Diseases and Science, vol. 26, No. 7, Supplement 1981, pp. 31s–40s.

Auth, D.C., "Animal Testing of Endoscopic Hemostasis with Lasers and Other Devices," Endoscopy, vol. 18, Supplement 2, May 1986, pp. 36–39.

McLean, A. J., "The Bovie Electrosurgical Current Generator—Some Underlying Principles and Results," Archives of Surgery, vol. 18, 1929, pp. 1863–1873.

Mclean, A. J., "Characteristics of Adequate Electrosurgical Current," American Journal of Surgery, vol. XVIII, No. 3, Feb. 16, 1932, pp. 417–441.

Wattiez, Arnaud et al., Electrosurgery in Operative Endoscopy, Blackwell Science Ltd., London, 1995, pp. 87–93, 155–163.

Farin, G., "Pneumatically Controlled Bipolar Cutting Instrument," End. Surg., 1993, pp. 1–3.

Muller, W., "The Advantages of Laparoscopic Assisted Bipolar High–Frequency Surgery," End. Surg., 1993, pp. 1–6.

Reidenbach, H. D., "Fundamentals of Bipolar High–Frequency Surgery," End Surg. 1993, pp. 85–90.

Penketh, Richard et al., "Clinical Evaluation of the Procision Bipolar Electrosurgical Generator During Laparoscopic Gynaecological Procedures," EAES, $2^{nd}$ International Congress of the European Association for Endoscopic Surgery, Madrid, Sep. 15–17, 1994.

Lloyd, David M. et al., "A New Portable Bipolar Generator–Use in Laparoscopic Cholecystectomy," EAES, $2^{nd}$ International Congress of the European Association for Endoscopic Surgery, Madrid, Sep. 15–17, 1994.

Buchelt, Martin et al., "Excimer Laser Ablation of Fibrocartilage: An In Vitro and In Vivo Study," Lasers in Surgery and Medicine, vol. 11, 1991, pp. 271–279.

Srinivasan, R., "Ablation of Polymers and Biological Tissue by Ultraviolet Lasers," Science, vol. 234, Oct. 31, 1986, pp. 559–565.

Pearce, John A., "Chapter 3 Electrosurgery," *Handbook of Biomedical Engineering,* Ed. Jacob Kline, Academic Press, Inc., 1988, pp. 99–113.

Selikowitz, Stuart M. et al., "Electric Current and Voltage Recordings on the Myocardium During Electrosurgical Procedures in Canines," *Reprint from Surgery, Gynecology & Obstetrics,* Mar. 1987, vol. 164, pp. 219–224.

Tucker, Robert D. et al., "Demodulated Low Frequency Currents from Electrosurgical Procedures," Surgery, Gynecology & Obstetrics, Jul. 1984, vol. 159, pp. 39–43.

Lu, David Y. et al., "Electrical Thermal Angioplasty: Catheter Design Features, In Vitro Tissue Ablation Studies and in Vivo Experimental Findings," Am J Cardiol, vol. 60, 1987, pp. 1117–1122.

Malis, Leonard I., "Electrosurgery: Technical Note," J. Neurosurg., vol. 85, 1996, pp. 970–975.

Slager, C. J. et al., "Spark Erosion of Arteriosclerotic Plaques," Kardiologie, vol. 76, Suppl. 6, 1987, pp. 67–71.

Geddes, Leslie A., *Medical Device Accidents—With Illustrative Cases,* CRC Press, New York, 1998, p. 93 (commentary on Honig, William M., "The Mechanism of Cutting in Electrosurgery," IEEE Transactions on Biomedical Engineering, Jan. 1975, pp. 58–65).

Valleylab, Inc., "Force Electrosurgical Generators Instruction Manual," Valleylab Part No. 945 110 039 A, Feb. 1987, pp. 59–62.

Valleylab, Inc., "Advances in Bipolar Electrosurgery for Laparoscopic Surgery," Advances in Bipolar Electrosurgery, pp. 1–4.

Description of Codman and Johnson & Johnson Malis CMC–III Bipolar System.

Pfizer/Valleylab Press Release "Valleylab Inc. Introduces The Procision Bipolar Electrosurgery System," Sep. 15, 1994.

ArthroCare Corporation, "ArthroCare Arthroscopic Electrosurgery System, Model 970 Operator's Manual," Feb. 1996.

ELECTROSURGICAL INSTRUMENT

BACKGROUND OF THE INVENTION

This invention relates to an electrosurgical instrument for the treatment of tissue in the presence of an electrically conductive fluid medium, to electrosurgical apparatus including such an instrument, and to an electrode unit for use in such an instrument.

Endoscopic electrosurgery is useful for treating tissue in cavities of the body, and is normally performed in the presence of a distension medium. When the distension medium is a liquid, this is commonly referred to as underwater electrosurgery, this term denoting electrosurgery in which living tissue is treated using an electrosurgical instrument with a treatment electrode or electrodes immersed in liquid at the operation site. A gaseous medium is commonly employed when endoscopic surgery is performed in a distensible body cavity of larger potential volume in which a liquid medium would be unsuitable, as is often the case in laparoscopic or gastroenterological surgery.

Underwater surgery is commonly performed using endoscopic techniques, in which the endoscope itself may provide a conduit (commonly referred to as a working channel) for the passage of an electrode. Alternatively, the endoscope may be specifically adapted (as in a resectoscope) to include means for mounting an electrode, or the electrode may be introduced into a body cavity via a separate access means at an angle with respect to the endoscope—a technique commonly referred to as triangulation. These variations in technique can be subdivided by surgical speciality, where one or other of the techniques has particular advantages given the access route to the specific body cavity. Endoscopes with integral working channels, or those characterised as resectoscopes, are generally employed when the body cavity may be accessed through a natural body opening—such as the cervical canal to access the endometrial cavity of the uterus, or the urethra to access the prostate gland and the bladder. Endoscopes specifically designed for use in the endometrial cavity are referred to as hysteroscopes, and those designed for use in the urinary tract include cystoscopes, urethroscopes and resectoscopes. The procedures of transurethal resection or vaporisation of the prostate gland are known as TURP and EVAP respectively. When there is no natural body opening through which an endoscope may be passed, the technique of triangulation is commonly employed. Triangulation is commonly used during underwater endoscopic surgery on joint cavities such as the knee and the shoulder. The endoscope used in these procedures is commonly referred to as an arthroscope.

Electrosurgery is usually carried out using either a monopolar instrument or a bipolar instrument. With monopolar electrosurgery, an active electrode is used in the operating region, and a conductive return plate is secured to the patient's skin. With this arrangement, current passes from the active electrode through the patient's tissues to the external return plate. Since the patient represents a significant portion of the circuit, input power levels have to be high (typically 150 to 250 watts), to compensate for the resistive current limiting of the patient's tissues and, in the case of underwater electrosurgery, power losses due to the fluid medium which is rendered partially conductive by the presence of blood or other body fluids. Using high power with a monopolar arrangement is also hazardous, due to the tissue heating that occurs at the return plate, which can cause severe skin burns. There is also the risk of capacitive coupling between the instrument and patient tissues at the entry point into the body cavity.

With bipolar electrosurgery, a pair of electrodes (an active electrode and a return electrode) are used together at the tissue application site. This arrangement has advantages from the safety standpoint, due to the relative proximity of the two electrodes so that radio frequency currents are limited to the region between the electrodes. However, the depth of effect is directly related to the distance between the two electrodes; and, in applications requiring very small electrodes, the inter-electrode spacing becomes very small, thereby limiting tissue effect and the output power. Spacing the electrodes further apart would often obscure vision of the application site, and would require a modification in surgical technique to ensure direct contact of both electrodes with the tissue.

There are a number of variations to the basic design of the bipolar probe. For example, U.S. Patent Specification No. 4706667 describes one of the fundamentals of the design, namely that the ratio of the contact areas of the return electrode and of the active electrode is greater than 7:1 and smaller than 20:1 for cutting purposes. This range relates only to cutting electrode configurations. When a bipolar instrument is used for desiccation or coagulation, the ratio of the contact areas of the two electrodes may be reduced to approximately 1:1 to avoid differential electrical stresses occurring at the contact between the tissue and the electrode.

The electrical junction between the return electrode and tissue can be supported by wetting of the tissue by a conductive solution such as normal saline. This ensures that the surgical effect is limited to the needle or active electrode, with the electric circuit between the two electrodes being completed by the tissue. One of the obvious limitations with the design is that the needle must be completely buried in the tissue to enable the return electrode to complete the circuit. Another problem is one of the orientation: even a relatively small change in application angle from the ideal perpendicular contact with respect to the tissue surface, will change the contact area ratio, so that a surgical effect can occur in the tissue in contact with the return electrode.

Cavity distension provides space for gaining access to the operation site, to improve visualisation, and to allow for manipulation of instruments. In low volume body cavities, particularly where it is desirable to distend the cavity under higher pressure, liquid rather than gas is more commonly used due to better optical characteristics, and because it washes blood away from the operative site.

Conventional underwater electrosurgery has been performed using a non-conductive liquid (such as 1.5% glycine) as an irrigant, or as a distension medium to eliminate electrical conduction losses. Glycine is used in isotonic concentrations to prevent osmotic changes in the blood when intra-vascular absorption occurs. In the course of an operation, veins may be severed, with resultant infusion of the liquid into the circulation, which could cause, among other things, a dilution of serum sodium which can lead to a condition known as water intoxication.

The applicants have found that it is possible to use a conductive liquid medium, such as normal saline, in underwater endoscopic electrosurgery in place of non-conductive, electrolyte-free solutions. Normal saline is the preferred distension medium in underwater endoscopic surgery when electrosurgery is not contemplated, or a non-electrical tissue effect such as laser treatment is being used. Although normal saline (0.9% w/v; 150 mmol/l) has an electrical conductivity somewhat greater than that of most body tissue, it has the advantage that displacement by absorption or extravasation from the operative site produces little physiological effect, and the so-called water intoxication effects of non-conductive, electrolyte-free solutions are avoided.

The applicants have developed a bipolar instrument suitable for underwater electrosurgery using a conductive liquid or gaseous medium. This electrosurgical instrument for the treatment of tissue in the presence of a fluid medium, comprises an instrument body having a handpiece and an instrument shaft and an electrode assembly, at one end of the shaft. The electrode assembly comprises a tissue treatment electrode which is exposed at the extreme distal end of the instrument, and a return electrode which is electrically insulated from the tissue treatment electrode and has a fluid contact surface spaced proximally from the exposed part of the tissue treatment electrode. In use of the instrument, the tissue treatment electrode is applied to the tissue to be treated whilst the return electrode, being spaced proximally from the exposed part of the tissue treatment electrode, is normally spaced from the tissue and serves to complete an electrosurgical current loop from the tissue treatment electrode through the tissue and the fluid medium. This electrosurgical instrument is described in the specification of the applicants' co-pending International Patent Application No. PCT/GB96/01473.

The electrode structure of this instrument, in combination with an electrically-conductive fluid medium largely avoids the problems experienced with monopolar or bipolar electrosurgery. In particular, input power levels are much lower than those generally necessary with a monopolar arrangement (typically 100 watts). Moreover, because of the relatively large spacing between its electrodes, an improved depth of effect is obtained compared with conventional bipolar arrangements.

An arthroscope electrode may be characterised as short (100 to 140 mm), and rigid with a working diameter up to 5 mm. It can be introduced through a stab incision into a joint cavity (with or without a cannula) using the triangulation technique. Such an electrode is operated with a motion which moves the electrode between the 9 O'Clock and 3 O'Clock positions on the arthroscopic image. As a result, the tissue to be treated is usually approached at a shallow working angle with respect to the axis of the electrode. An arthroscopic electrode thus needs to have an effect consistent with this angled approach to the tissue. The tissue to be treated, such as meniscal cartilage, is commonly dense and of a high electrical impedance. An arthroscope electrode requires output power and voltage settings that reflect the type of tissue being treated, the size of electrode, and the fact that arthroscopists are seeking a speed of effect comparable to that of the mechanical shaver devices they currently employ, albeit with an electrode of smaller dimensions than a shaver blade for improved access. Joint spaces are commonly small (the joint spaces in the knee being typically 60 to 100 mls under fluid distension), and tissue often needs mechanical manipulation. Known monopolar arthroscopic electrode configurations, therefore, are of a rigid construction, having angled hook or probe-tip configurations to produce cutting of high impedance tissue, and to connect to an ergonomic handpiece to aid tissue manipulation.

The aim of the invention is to provide an improved electrosurgical instrument of this type.

SUMMARY OF THE INVENTION

The present invention provides an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed end extending laterally through a cut-out provided in the insulation member at the distal end portion of the instrument, and the return electrode having a fluid contact surface which overlies the insulation member in the region of the cut-out, said fluid contact surface being spaced from the tissue treatment electrode in such a manner as to define, in use, a conductive fluid path that completes an electrical circuit between the tissue treatment electrode and the return electrode.

The invention also provides an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed end extending laterally through a cut-out provided in the insulation member, wherein the return electrode has a distal end portion with a fluid contact surface which overlies the insulation member in the region of the cut-out and faces laterally in a first direction, and wherein the insulation member projects laterally outwardly between said distal end portion and the tissue treatment electrode, the tissue treatment electrode facing laterally in a second direction opposite to said first direction.

The laterally projecting part of the insulation member increases the conductive fluid path length from the tissue treatment electrode to the return electrode, and forces the electric field outwardly, thereby preventing preferential arcing between the return electrode and the nearest part of the tissue treatment electrode, and promoting arcing between the tissue treatment electrode and the neighboring tissue.

The return electrode is spaced from the tissue treatment electrode so that, in use, it does not contact the tissue to be treated, and so that the electrical circuit is always completed by the conductive fluid, and not simply by arcing between the electrodes. Indeed, the arrangement is such that arcing between adjacent parts of the electrode assembly is avoided, thereby ensuring that the tissue treatment electrode can become enveloped in a vapour pocket so that tissue entering the vapour pocket becomes the preferred path for current to flow back to the return electrode via the conductive fluid.

The electrosurgical instrument of the invention is useful for dissection, resection, vaporisation, desiccation and coagulation of tissue, as well as for combinations of these functions. It has a particular application in arthroscopic surgery as it pertains to endoscopic and percutaneous procedures performed on joints of the body including, but not limited to, such techniques as they apply to the spine and other non-synovial joints. Arthroscopic operative procedures may include: partial or complete meniscectomy of the knee joint including meniscal cystectomy; lateral retinacular release of the knee joint; removal of anterior and posterior cruciate ligaments or remnants thereof; labral tear resection, acromioplasty, bursectomy and subacromial decompression of the shoulder joint; anterior release of the temperomandibular joint; synovectomy, cartilage debridement, chondroplasty, division of intra-articular adhesions, fracture and tendon debridement as applied to any of the synovial joints of the body; inducing thermal shrinkage of joint capsules as a treatment for recurrent dislocation, subluxation or repetitive stress injury to any articulated joint of the body;

discectomy either in the treatment of a disc prolapse or as part of a spinal fusion via a posterior or anterior approach to the cervical, thoracic and lumbar spine or any other fibrous joint for similar purposes; excision of diseased tissue; and haemostasis.

The instrument of the invention is also useful for dissection, resection, vaporisation, desiccation and coagulation of tissue, as well as combinations of these functions, with particular application in urological endoscopic (urethroscopy, cystoscopy, ureteroscopy and nephroscopy) and percutaneous surgery. Urological procedures may include: electro-vaporisation of the prostate gland (EVAP) and other variants of the procedure commonly referred to as transurethral resection of the prostate (TURP) including, but not limited to, interstitial ablation of the prostate gland by a percutaneous or perurethral route whether performed for benign or malignant disease; transurethral or percutaneous resection of urinary tract tumours as they may arise as primary or secondary neoplasms, and further as they may arise anywhere in the urological tract from the calyces of the kidney to the external urethral meatus; division of strictures as they may arise at the pelviureteric junction (PUJ), ureter, ureteral orifice, bladder neck or urethra; correction of ureterocoele; shrinkage of bladder diverticular; cystoplasty procedures as they pertain to corrections of voiding dysfunction; thermally induced shrinkage of the pelvic floor as a corrective treatment for bladder neck descent; excision of diseased tissue; and haemostasis.

Surgical procedures using the electrosurgical instrument of the invention may also include introducing the electrode assembly to the surgical site, whether through an artificial conduit (a cannula) or a natural conduit, which may be in an anatomical body cavity or space, or one created surgically. The cavity or space may be distended during the procedure using a fluid, or may be naturally held open by anatomical structures. The surgical site may be bathed in a continuous flow of conductive fluid such as saline solution either to fill and distend the cavity, or to create a locally-irrigated environment around the tip of the electrode assembly in a gas filled cavity. The irrigating fluid may be aspirated from the surgical site to remove products created by application of the RF energy, tissue debris or blood. The procedures may include simultaneous viewing of the site via an endoscope, or using an indirect visualisation means. An irrigated bipolar electrosurgical instrument is described in the specification of our co-pending International Patent Application No. PCT/GB96/01472.

Advantageously, the exposed end of the tissue treatment electrode is constituted by a plurality of tissue contact filamentary members made of an electrically-conductive material, the filamentary members being electrically connected to a common electrical supply conductor.

In a preferred embodiment, a single coiled filament constitutes the filamentary members, the coils of the filament constituting the filamentary members. The filament may have a diameter lying in the range of from 0.05 mm to 0.5 mm.

In another preferred embodiment, a plurality of separate, individual filaments constitute the filamentary members. The filaments may each have a length lying within the range of from 0.5 mm to 5 mm, and a diameter lying within the range of from 0.05 mm to 0.5 mm.

Preferably, the filamentary members are made of tungsten, or of an alloy of tungsten or platinum.

Alternatively, the exposed end of the tissue contact electrode is constituted by a mesh.

Preferably, the instrument further comprises suction means for applying a sub-atmospheric pressure to the interior of the insulation member, whereby vapour bubbles produced in the region of the tissue treatment electrode are evacuated via the interior of the instrument.

Advantageously, the cut-out is formed in a lateral surface of the insulation member adjacent to the distal end thereof. In this case, the instrument can be used as a sideeffect instrument. Alternatively, the cut-out is formed obliquely across the distal end face of the insulation member, whereby the exposed end of the tissue treatment electrode has both an axially-facing tissue contact portion and a laterally-facing tissue contact portion. In this case, the instrument can be used as both an end-effect instrument and as a side-effect instrument.

Advantageously, the dimensions and configuration of the tissue treatment electrode, the fluid contact surface and the insulation member are such that, when the electrode assembly is immersed in a conductive fluid medium, the ratio of (i) the length of the shortest conductive path through the fluid medium between the fluid contact surface and that part of the tissue treatment electrode which is furthest from the fluid contact surface, to (ii) the length of the shortest conduction path through the fluid medium between the fluid contact surface and the tissue treatment electrode is at most 2 to 1.

Preferably, the laterally-projecting portion of the insulation member defines an insulation barrier to divert electrical current flow through the fluid medium thereby to increase said shortest conduction path length between the fluid contact surface and the tissue treatment electrode. The first direction may define a treatment axis, and said two shortest conductive paths may lie in a common plane containing the treatment axis.

The invention also provides an electrode unit for an electrosurgical instrument for the treatment of tissue in the presence of an electrically-conductive fluid medium, the electrode unit comprising a shaft having at one end means for connection to an instrument handpiece, and, mounted on the other end of the shaft, an electrode assembly comprising a tissue treatment electrode and a return electrode which is electrically insulated from the tissue treatment electrode by means of an insulation member, the tissue treatment electrode having an exposed end extending laterally through a cut-out provided in the insulation member, and the return electrode having a fluid contact surface which overlies the insulation member in the region of the cut-out, said fluid contact surface being spaced from the tissue treatment electrode in such a manner as to define, in use, a conductive fluid path that completes an electrical circuit between the tissue treatment electrode and the return electrode.

The invention further provides electrosurgical apparatus comprising a radio frequency generator and an electrosurgical instrument for the treatment of tissue in the presence of an electrically-conductive fluid medium, the instrument comprising an instrument shaft, and an electrode assembly at one end of the shaft, the electrode assembly comprising a tissue treatment electrode and a return electrode which is electrically insulated from the tissue treatment electrode by means of an insulation member, the tissue treatment electrode having an exposed end extending laterally through a cut-out provided in the insulation member at the distal end portion of the instrument, the return electrode having a fluid contact surface which overlies the insulation member in the region of the cut-out, and the radio frequency generator having a bipolar output connected to the electrodes, said fluid contact surface being spaced from the tissue treatment electrode in such a manner as to define, in use, a conductive fluid path that completes an electrical circuit between the tissue treatment electrode and the return electrode.

Advantageously, the radio frequency generator includes controller for varying the output power delivered to the electrodes. The controller may be such as to provide output power in first and second output ranges, the first output range being for powering the electrosurgical instrument for tissue desiccation, and the second output range being for powering the electrosurgical instrument for tissue removal by cutting or vaporisation. Conveniently, the first output range is from about 150 volts to 200 volts, and the second output range is from about 250 volts to 600 volts, the voltages being peak voltages.

Preferably, the controller is such as to alternate the output power between first and second powers in the first and second output ranges. Alternatively, the controller is such as to pulse the output power at a power within the second output range.

The invention still further provides an electrosurgical method comprising the steps of: providing an electrosurgical apparatus having at least at tissue desiccation mode and a tissue vaporisation mode, the apparatus having a radio frequency generator coupled to an electrode assembly for the treatment of tissue in the presence of an electricallyconductive fluid medium, the electrode assembly comprising a tissue treatment electrode and a return electrode which is electrically insulated from the tissue treatment electrode by means of an insulation member, the tissue treatment electrode having an exposed and extending laterally through a cut out provided in the insulation member at distal end of the assembly and the return electrode having a fluid contact surface spaced from the exposed end of the tissue treatment electrode by the insulation member; introducing the electrode assembly into a selected operation site with the tissue treatment electrode adjacent to the tissue to be treated;

immersing the fluid contact surface of the return electrode and the exposed end of the tissue treatment electrode in electrically-conductive fluid; and controlling the output power of the radio frequency generator to lie within a first output range for the tissue desiccation mode and to lie within a second range for the tissue vaporisation mode, the first output range being such that the power supplied to the electrode assembly maintains the conductive fluid adjacent to the tissue treatment electrode substantially at boiling point for tissue desiccation without creating a vapour pocket surrounding the tissue treatment electrode, and the second output range is such that the output power supplied to the electrode assembly for vaporisation of tissue is such as to maintain a vapour pocket surrounding the tissue treatment electrode.

Advantageously, the first output range is from about 150 volts to 200 volts and the second output range is from about 250 volts to 600 volts, the voltages being peak voltages.

Preferably, the electrode assembly is introduced into the selected operation site in a direction which is generally along the surface of the tissue to be treated, and with the tissue treatment electrode facing the tissue to be treated.

BRIEF DESCRIPTION OF THE DRAWINGS

The invention will now be described in greater detail, by way of example with reference to the drawings, in which.

DETAILED DESCRIPTION OF THE DRAWINGS

Each of the electrode units described below is intended to be used with a conductive distension medium such as normal saline, and each unit has a dual-electrode structure, with the conductive medium acting as a conductor between the tissue being treated and one of the electrodes, hereinafter called the return electrode. The other electrode is applied directly to the tissue, and is hereinafter called the tissue treatment (active) electrode. In many cases, the use of a liquid distension medium is preferable, as it prevents excessive electrode temperatures in most circumstances, and largely eliminates tissue sticking.

Figure 1:
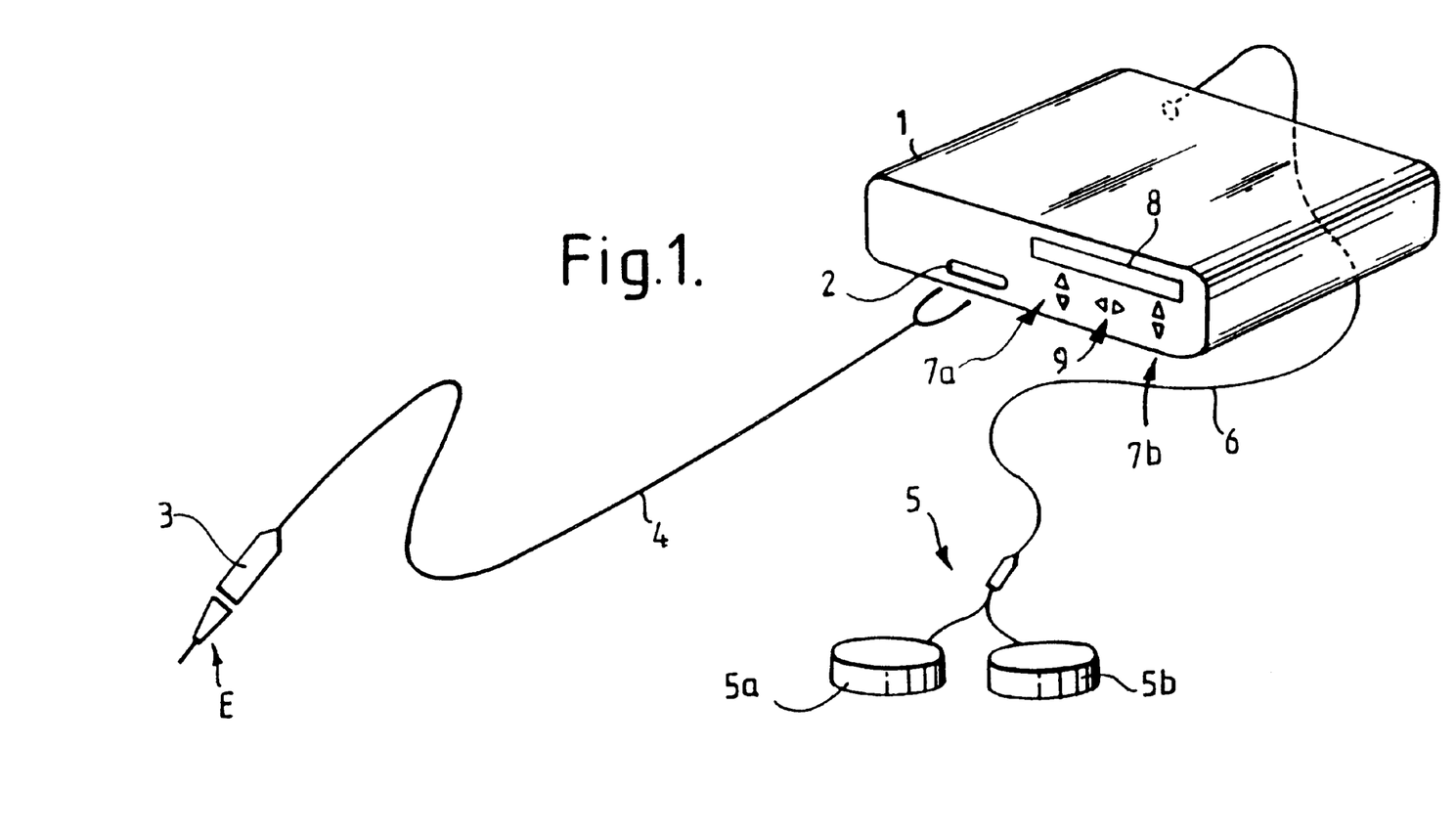
FIG. 1 is a diagram showing an electrosurgical apparatus constructed in accordance with the invention.

Referring to the drawings, FIG. 1 shows electrosurgical apparatus including a generator 1 having an output socket 2 providing a radio frequency (RF) output for an instrument in the form of a handpiece 3 via a connection cord 4. Activation of the generator 1 may be performed from the handpiece 3 via a control connection in the cord 4, or by means of a footswitch unit 5, as shown, connected separately to the rear of the generator 1 by a footswitch connection cord 6. In the illustrated embodiment, the footswitch unit 5 has two footswitches 5a and 5b for selecting a desiccation mode and a vaporisation mode of the generator 1 respectively. The generator front panel has push buttons 7a and 7b for respectively setting desiccation and vaporisation power levels, which are indicated in a display 8. Push buttons 9a are provided as an alternative means for selection between the desiccation and vaporisation modes.

The handpiece 3 mounts a detachable electrode unit E, such as the electrode units E1 to E5 to be described below.

Figure 2:
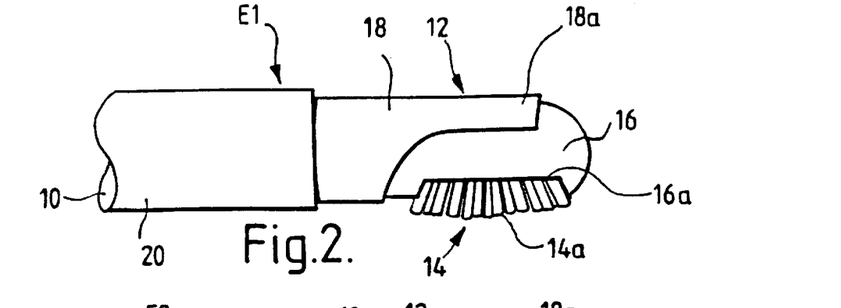
FIGS. 2 to 6 are diagrammatic side elevations of the electrode assemblies of five forms of electrode unit constructed in accordance with the inventions.

FIG. 2 shows the first form of electrode unit E1 for detachable fastening to the electrosurgical instrument handpiece 3, the electrode unit comprising a shaft 10, which is constituted by a semi-flexible tube made of stainless steel or phynox electroplated in copper or gold, with an electrode assembly 12 at a distal end thereof. At the other end (not shown) of the shaft 10, means are provided for connecting the electrode unit E1 to the handpiece 3 both mechanically and electrically.

The RF generator 1 (not shown in FIG. 2) delivers an electrosurgical current to the electrode assembly 12. The generator includes means for varying the delivered output power to suit different electrosurgical requirements. The generator may be as described in the specification of our co-pending European Patent Application 96304558.8.

The electrode unit E1 includes an active electrode 14 which is constituted by a plurality of filaments made of tungsten or an alloy of tungsten or platinum. The active (brush) electrode 14 is connected to the RF generator 1 via an insulated central copper conductor (not shown). A ceramic insulation sleeve 16 surrounds the central conductor, the filaments 14a of the brush electrode passing along the insulation sleeve and extending laterally therefrom through a cut-out 16a. A return electrode 18, which is constituted by the distal end of the instrument shaft, surrounds the proximal end of the sleeve 16. An outer insulating coating 20 (which could be polyvinylidene fluoride, a polyimide, polytetrafluoroethylene, a polyolefin, a polyester or ethylene tetrafluoroethylene) surrounds the proximal portion of the shaft adjacent to the return electrode 18. The return electrode 18 is formed with a hood-like extension 18a which extends over the surface of the sleeve 16 which is opposite to the cut-out 16a. The electrode unit E1 can, thus, provide maximum tissue engagement for shallow working angle applications, and is known as a side-effect electrode.

This electrosurgical instrument is particularly useful for rapid tissue debulking. One of the problems which could be encountered when tissue is rapidly debulked using an arthroscopic electrode configuration, particularly when working in small joint spaces, is the production of vapour bubbles generated as an end product of tissue vaporisation.

Such bubbles obscure vision, and can coalesce at the site of tissue application, so that the electrical circuit between the active and return electrodes becomes compromised by the absence of conductive fluid. Irregular active electrodes having filamentary, mesh or coiled spring forms go some way to solving this problem as they reduce the vaporisation threshold as disclosed in the specifications of our co-pending British patent applications Nos. 9600354.6, 9619015.2 and 9619999.7 Another advantage of these electrode forms is that the bubbles generated by vaporisation are smaller than those formed by solid electrodes. As the brush electrode 14 of this electrosurgical instrument is of irregular shape, it also has the advantage of producing relatively small vapour bubbles as the product of tissue vaporisation. The production of vapour bubbles is, however, further reduced as a result of the lower threshold power of vaporisation which results from use of the electrode unit E1. This improvement results from the hood-like extension 18a of the return electrode 18 which extends over the back of the active electrode 14a. This reduces the separation between the active electrode 14 and the return electrode 18, thereby reducing the electrical field and the vaporisation threshold power of the active electrode. This enhances the speed of vaporisation of the tissue at a lower power than would otherwise be required for the given active electrode area, and hence reduces the formation of vapour bubbles. As the hood-like extension 18a extends along the entire length of the active electrode 14, a large active electrode size can be supported, despite the reduction in electrode separation.

The robustness of the electrode assembly 12 is also important in arthroscopic surgery, both because of the tendency of surgeons to use an electrode assembly as a cold manipulator, and because of the rigid nature of the tissue to be treated—particularly bone and cartilage. The hood-like extension 18a adds mechanical strength to the electrode assembly 12, as it extends over the ceramic insulation sleeve 16, thereby reducing the risk of ceramic fracture and potential breakdown of insulation.

The electrode unit E1 is intended primarily for use in arthroscopic surgery which requires rapid tissue debulking by vaporisation. In use, the electrosurgical instrument is manipulated to introduce the electrode assembly 12 into a selected operation site (for example, within the joint space of a knee), so that the brush electrode 14 contacts the tissue to be treated, and with the tissue and the electrode assembly immersed in saline.

The footswitch 5b (or the push button 7b) is then operated to set the required power level for vaporisation. The generator 1 then provides sufficient RF power to the electrode assembly 12 to vaporise the saline surrounding the brush electrode 14, and to maintain a vapour pocket surrounding this electrode. Using a brushing technique, with firm pressure against the tissue surface, rapid debulking of the tissue is achieved. Gently touching the tissue will reduce the effect, and can be used to sculpture and smooth the residual tissue surface.

Because of its speed of debulking and side-effect configuration, the electrode unit E1 also has advantages in urological surgery as an EVAP technique for use in conjunction with a resectoscope. A resectoscope electrode unit is introduced very differently, in that it is mounted on an endoscope prior to passage of the assembled instrument through a working sheath introduced via the urethra. The proximal end of the electrode unit is connected to a trigger assembly and an electrical contact which is integral with the resectoscope. By this means, the electrode unit can be moved back and forth through a defined range of motion by operating the trigger mechanism. As the electrode unit is assembled prior to introduction, the size of the tip is not constrained by working channel dimensions, but rather by the diameter of the working sheath which can be up to 10 mm. Part of this diameter is occupied by the support wires to the electrode unit, which wires are commonly bent in a downward angle, with respect to the endoscopic image, to the working tip, so that they do not interfere with either visualisation or its operation. The brush electrode 14 can have a length lying within the range of from 3 mm to 4 mm and a width lying in the range of from 2 mm to 3 mm, and this size is necessary for urological surgery given that, on average, 20–30 grams of prostate tissue must be removed.

Because of the reservoir effect of the urinary bladder, and the mounting of the endoscope to view the tip of the active electrode from below, bubble generation during vaporisation is less of a problem during endoscopic urology, as the bubbles flow away from the endoscope to accumulate in the bladder. Nevertheless, the use of the electrode unit E1 substantially reduces the possibility of bubble generation causing problems.

Although the electrode unit E1 is intended primarily for use in the vaporisation of tissue, it can also be used for desiccation, particularly of synovial membranes or to separate muscle attachments. In this case, once the electrode assembly 12 has been introduced into a selected operation site, the RF generator 1 is actuated using the footswitch 5a or the push button 7a to set the required power level for desiccation. The generator will then provide sufficient RF power to the electrode assembly 12 to maintain the saline adjacent to the brush electrode 14 substantially at its boiling point without creating a vapour pocket surrounding that electrode. The instrument can then be manipulated by moving the brush electrode 14 across the surface of the tissue to be treated in a side-to-side "painting" technique.

The electrode unit E1 can also be used for blending tissue. Thus, by automatically alternating the output of the RF generator 1 between the desiccation and vaporisation power levels, more haemostasis is produced then is possible in the vaporisation mode. As a consequence, the speed of tissue debulking can be reduced, which is useful when cutting or debulking vascular tissue structures. Alternatively, the output of the RF generator 1 can be pulsed at the vaporisation power level, without cycled activation of the desiccation mode. This produces a less aggressive tissue vaporisation than occurs in the vaporisation mode, with a consequent reduction in both bubble formation and the risk of tissue charring.

FIGS. 3 to 6 show electrode units E2 to E5 which are modified versions of the electrode E1. Accordingly, like reference numerals will be used for like parts, and only the modifications will be described in detail. Thus, the active electrode 14 of the electrode unit E2 is a coiled-spring electrode mounted within the cut-out 16a. The coiled spring electrode 14 is made of tungsten or an alloy of tungsten or platinum, and its proximal end is connected to the RF generator 1 via an insulated central copper conductor (not shown).

Figure 4:
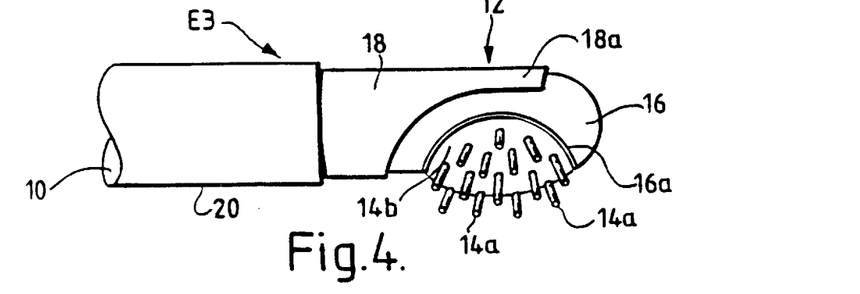

The electrode unit E3 of FIG. 4 is of "sputnik" form, having an active electrode 14 constituted by a plurality of needle-like protrusions 14a extending from a thin metal base plate 14b mounted within the cut-out 16a in the insulation sleeve 16. Both the base plate 14b, and the protrusions 14a are made of tungsten or an alloy of tungsten or platinum. The needle-like protrusions 14a are connected to the RF generator 1 via a common insulated central copper conductor (not shown). This unit E3 is less complex to manufacture as compared with the brush-type form of the unit E1, and will produce similar effects. Moreover, it allows for variations in the density of the needle-like protrusions 14a over the area of the base plate 14b.

Figure 5:
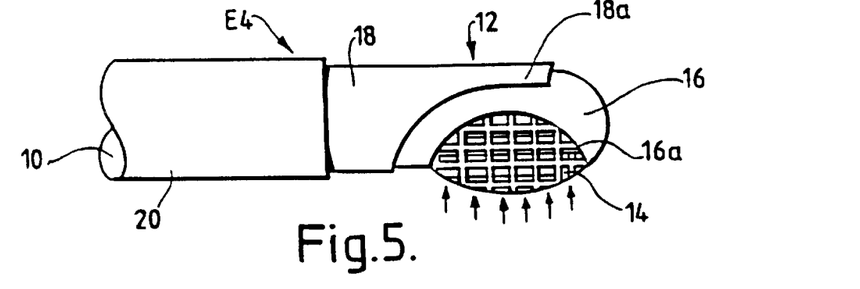

FIG. 5 shows the electrode unit E4 having an active electrode 14 which is constituted by a mesh made of tungsten or an alloy of tungsten or platinum. This electrode unit E4 can be provided with a suction pump (not shown) which can remove vapour bubbles via the shaft of the instrument through the active electrode 14. This enhances the elimination of vapour bubbles from an operation site, which is particularly advantageous during aggressive tissue debulking. The suction pump must be controlled so that the flow of bubbles through the electrode 14 is balanced to the output characteristics of the RF generator 1 to prevent excessive cooling of the active electrode and a resultant increase in its vaporisation power threshold. The thermal mass of the mesh active electrode 14 is lower than that of a solid form active electrode, and this assists in rapidly re-establishing the vapour pocket around the active electrode should this collapse following excessive cooling. The control means for the suction pump may involve the use of an intermittent suction technique.

Figure 6:
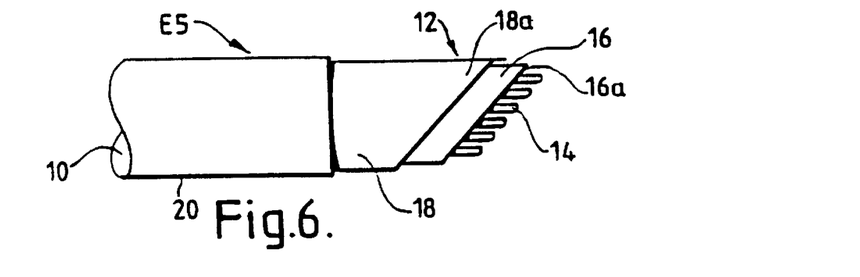

FIG. 6 shows the electrode unit E5 having an active electrode 14 of the coiled spring type. Here, however, the cut-out 16a is formed obliquely (at 45°) across the distal end face of the insulation sleeve 16, so that the exposed end of the active electrode 14 has both an axially-facing tissue contact portion and a laterally-facing tissue contact portion. The tip of the coiled electrode 14 is also angled at 45 degrees to the axis of the instrument, so that this electrode unit is both an end effect electrode and a side effect electrode. The main advantage of this electrode unit E5 is that it can be used in conjunction with endoscopic surgery techniques which require working channel introduction.

Figure 3:
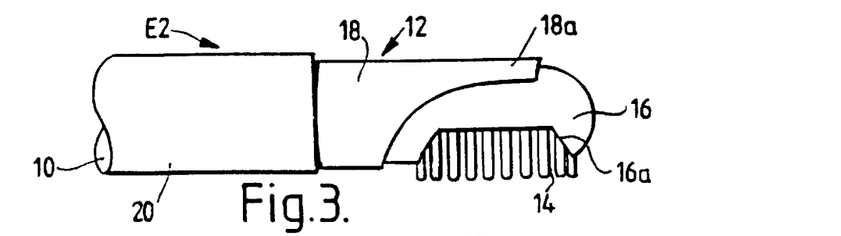
Figure 7:
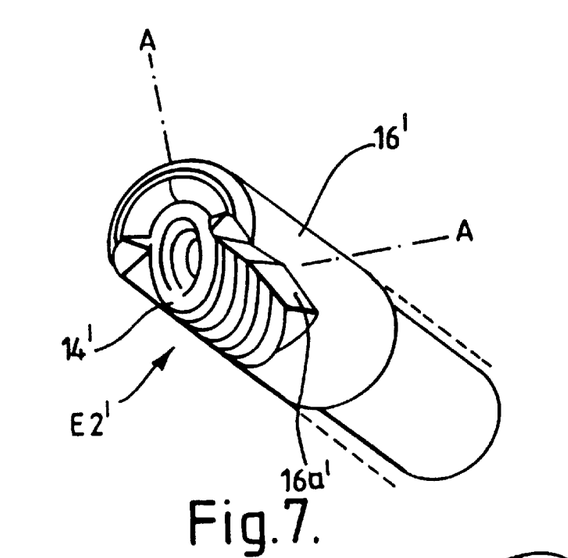
FIG. 7 is a perspective view of a modified form of the electrode assembly of FIG. 3.
Figure 8:
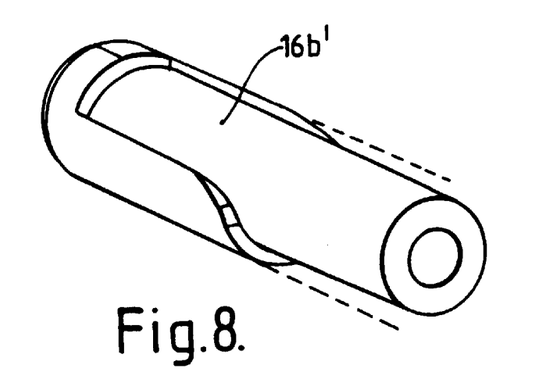
FIG. 8 is a perspective view of part of the assembly of FIG. 7.
Figure 9:
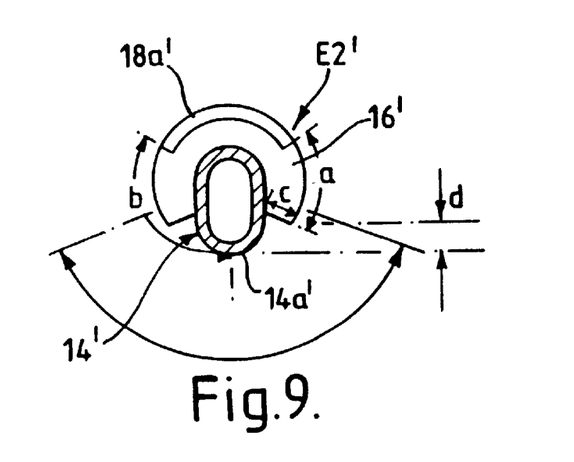
FIG. 9 is a cross-section taken on the lines A—A of FIG. 7.

The FIGS. 7 to 9 show a modified form of the electrode unit E2 of FIG. 3. This electrode unit E2' has an active electrode 14' in the form of a coiled-spring electrode mounted within a cut-out 16a' in the insulation member 16'. The coiled-spring electrode 14' is made of tungsten or an alloy of tungsten or platinum, and its proximal end is connected to the RF generator by an insulated central copper conductor (not shown). As shown in FIG. 8, the insulation member 16' is formed with a recess 16b' which receives the return electrode 18' and its extension 18a' (not shown in FIGS. 7 and 8).

As shown in FIG. 9, the active electrode 14' has a distal end portion which is exposed at the distal end of the instrument for tissue contact. This embodiment has advantages over the earlier embodiments, particularly where access is needed to remote areas of a joint cavity. Thus, in such remote joint cavity areas, the extension of the insulation member 16 of each of the embodiments of FIGS. 2 to 5 may prevent the associated active electrode 14 accessing these areas.

FIG. 9 illustrates the way in which the insulation member 16' projects laterally in the region between the active electrode 14' and the extension 18' of the return electrode 18'. This laterally projecting part of the insulation member 16' increases the conductive fluid path length from the active electrode 14' to the return electrode 18', and forces the electric field outwardly, thereby preventing preferential arcing between the return electrode and the nearest part of the active electrode, and promoting arcting between the active electrode and the neighboring tissue. The return electrode 18' is spaced from the active electrode 14' so that, in use, it does not contact the tissue to be treated, and so that the electrical circuit is always completed by the saline, and not simply arcing between the electrodes. Indeed, the arrangement is such that arcing between adjacent parts of the electrode assembly is avoided, thereby ensuring that the active electrode 14' can become enveloped in a vapour pocket, so that tissue entering the vapour pocket becomes the preferred path for current to flow back to the return electrode 18' via the conductive fluid.

To consider the operation of the electrode unit E2' in more detail, when it operates in a tissue cutting or vaporising mode, a vapour bubble is formed around the tip 14'a of the active electrode 14'. This tip 14'a constitutes an active electrode treatment portion. This bubble is sustained by arcing within it. The greater the applied voltage, the greater is the size of the bubble. The energy dissipated by each arc is impedancelimited by the remaining fluid in the conduction path and by the source impedance of the generator. However, an arc behaves as a negative impedance in that, if the energy in the arc is sufficiently high, an ionised path of very low impedance is formed. This can lead to an unstable condition of ever-decreasing ionised path impedance unless the impedance of the fluid between the bubble and the return electrode 18' is sufficient to act as a limit on dissipated power. It is also possible for the vapour pocket around the active electrode treatment portion 14'a to encroach the return electrode 18'. In these circumstances, the arc energy is limited only by generator source impedance, but such power limitation is poor and cannot be adjusted according to electrode size. For these reasons, the dimensions and configuration of the insulation member 16 should be such as to define a minimum conduction path length of 1mm between the active electrode treatment portion 14'a and the fluid contact surface of the return electrode 18'. This minimum path length is, in the case of the embodiment shown in FIG. 9, the arc length a of the insulation member 16' plus the step dimension c of the laterally projecting part of the insulation member.

A further consideration is the possibility of a vapour pocket forming only over part of the exposed treatment portion 14'a of the active electrode 14'. When the applied voltage and power are sufficiently high, a vapour pocket will form around the active electrode exposed treatment portion 14'a. Preferably, the pocket is formed uniformly over the entire length of the treatment portion. In such a situation, the load impedance presented to the generator can change by as much as a factor of 20. However, when there are significant differences in the conduction path length between the return electrode fluid contact surface 18a' and different parts of the exposed active electrode treatment portion 14'a, a voltage gradient is established over the length of each electrode. With some insulation member and active electrode configurations, the voltage gradient can be sufficiently large to enable vapour pocket formation only over that part of the exposed treatment portion closest to the fluid contact surface, leaving the extreme distal end of the exposed treatment portion still in contact with the conductive fluid. Thus, the voltage gradient is established within the conductive fluid where the edge of the vapour pocket intersects the surface of the active electrode treatment portion 14'a. The electrical behavior of such a partially-enveloped active electrode treatment portion 14'a is very different from that of a fully-enveloped treatment portion. In terms of controlling generator output by sensing peak voltage, the behavior of the electrode assembly is no longer bistable. However, the power demand is considerably higher as a result of the vaporisation voltage presented across the low impedance wetted region of the active electrode treatment portion 14'a. The clinical effect is not only the required vaporisation, but also an undesirable thermal damaging effect resulting from the increased power dissipation.

Partial enveloping of the active electrode treatment portion 14'a can be largely avoided by ensuring that the ratio of the length (b) of the conductive path between the furthermost point of the active electrode treatment portion and the length of the shortest conductive path between the active electrode treatment portion and the fluid contact surface is at most 2:1, ie b/(a+c)≦2. The laterally-projecting portion of the insulation member 16' defines an insulation barrier to direct electrical current flow through the fluid medium, thereby increasing the shortest conductive path between the fluid contact surface 18'a and the active electrode 14'.

It will be noted from FIG. 9 that the downward extent of the exposed active electrode treatment portion, ie. the distance d by which the active electrode projects beyond the shrouding parts of the insulation member 16' on each side, is at least one half of the width of the exposed treatment portion in a transverse plane. This allows the instrument to be rotated about the axis of its shaft to some extent without losing the required surgical effect.

FIG. 9 also shows that the active electrode 14' has an exposed end (the tip 14'a) which extends laterally through the cut-out 16'a in a first direction which is opposite to the direction in which the fluid contact surface 18a' faces. This first direction defines a treatment axis which lies in a common plane with the two shortest conductive paths referred to above. The electrode units of the embodiment of FIGS. 2 to 6 also include this future.

It should be noted that the insulation member 16 of each of the embodiments of FIGS. 2 to 6 also has laterally projecting part which increases the conductive fluid path length from the active electrode 14 to the return electrode 18. These electrode units also are such that the ratio of the length of the conductive path between the furthermost point of the active electrode treatment portion and the fluid contact surface of the return electrode, and the length of the shortest conductive path between the active electrode treatment portion and the fluid contact surface is at most 2:1.

In order further to improve access to remote joint cavity areas, the distal portion of the electrode shaft of each of the embodiments described above could be angled, say between 15° and 30°, with respect to the main portion of the instrument shaft. In a further modification, titanium could be used as the material for each of the active electrodes.

It will be apparent that modifications could be made to the embodiments described above. For example, the embodiments of FIGS. 1 to 4 and 6 could each be provided with a suction pump for removing vapour bubbles via the shaft of the instrument through the active electrode. It would also be possible to make the insulation sleeve 16 of each of the embodiments of a silicone rubber (such as a silicone polyurethane), glass, a polyimide or a thermoplastics material.

We claim:

1. An electrosurgical instrument for the treatment of tissue in the presence of an electrically-conductive fluid medium, the instrument having a distal end portion and comprising a semi-flexible instrument shaft capable of being used to exert firm pressure against tissue being treated by said instrument, and an electrode assembly at one end of the shaft, the electrode assembly comprising
    a tissue treatment electrode,
    a return electrode, and
    an insulation member electrically insulating the return electrode from the tissue treatment electrode, the tissue treatment electrode having an exposed end extending laterally through a cut-out provided in the insulation member at the distal end portion of the instrument, and the return electrode having a fluid contact surface which overlies the insulation member in the cut-out's region, said fluid contact surface being spaced from the tissue treatment electrode in such a manner as to define, in use, a conductive fluid path that completes an electrical circuit between the tissue treatment electrode and the return electrode, and wherein the treatment electrode and the return electrode are configured in an immovable relationship to one another and the instrument shaft.

2. An electrosurgical instrument as claimed in claim 1, wherein the exposed end of the tissue treatment electrode comprises a plurality of tissue contact filamentary members made of an electrically-conductive material, the filamentary members being electrically connected to a common electrical supply conductor.

3. An electrosurgical instrument as claimed in claim 2, wherein a single coiled filament constitutes the filamentary members, the coils of the filament constituting the filamentary members.

4. An electrosurgical instrument as claimed in claim 3, wherein the filament has a diameter lying within the range of from 0.05 mm to 0.5 mm.

5. An electrosurgical instrument as claimed in claim 2, wherein a plurality of separate, individual filaments constitute the filamentary members.

6. An electrosurgical instrument as claimed in claim 5, wherein the filaments each have a length lying within the range of from 0.5 mm to 5 mm.

7. An electrosurgical instrument as claimed in claim 5, wherein the filaments each have a diameter lying within the range of from 0.05 mm to 0.5 mm.

8. An electrosurgical instrument as claimed in claim 3, wherein the filamentary members are made of tungsten.

9. An electrosurgical instrument as claimed in claim 3, wherein the filamentary members are made of an alloy of tungsten or platinum.

10. An electrosurgical instrument as claimed in claim 1, wherein the exposed end of the tissue treatment electrode comprises a mesh.

11. An electrosurgical instrument as claimed in claim 1, further comprising suction means for applying a sub-atmospheric pressure to the insulation member's interior, whereby vapour bubbles produced in the region of the tissue treatment electrode are evacuated via the instrument's interior.

12. An electrosurgical instrument as claimed in claim 1, wherein the cut-out is formed in a lateral surface of the insulation member adjacent to a distal end thereof.

13. An electrosurgical instrument as claimed in claim 1, wherein the cut-out is formed obliquely across the distal end face of the insulation member, whereby the exposed end of the tissue treatment electrode has both an axially-facing tissue contact portion and a laterally-facing tissue contact portion.

14. An electrosurgical instrument as claimed in claim 1, wherein the tissue treatment electrode's dimensions and configuration, the fluid contact surface and the insulation member are such that, when the electrode assembly is immersed in a conductive fluid medium, a ratio of (i) a length of the shortest conduction path through the fluid medium between the fluid contact surface and that part of the tissue treatment electrode which is furthest from the fluid contact surface, to (ii) a length of the shortest conduction path through the fluid medium between the fluid contact surface and the tissue treatment electrode is at most 2 to 1.

15. An electrosurgical instrument as claimed in claim 14, wherein a ratio of (i) a length of a shortest conduction path through the fluid medium between the fluid contact surface and that part of the tissue treatment electrode which is furthest from the fluid contact surface, to (ii) a length of a shortest conduction path through the fluid medium between the fluid contact surface and the tissue treatment electrode is greater than or equal to 1.25.

16. An electrosurgical instrument as claimed in claim 1, wherein the tissue treatment electrode's dimensions and configuration, the fluid contact surface and the insulation member are such that, when the electrode assembly is immersed in a conductive fluid medium, a length of a shortest conduction path through the f fluid medium between the fluid contact surface and the tissue treatment electrode is at least 1 mm.

17. An electrosurgical instrument as claimed in claim 1, wherein the return electrode is in the form of a generally cylindrical conductive sleeve with an exposed surface portion having a length and a diameter, the length of the exposed surface portion being at least as great as the diameter, and wherein, when the electrode assembly is immersed in a conductive fluid medium, a ratio of (i) a shortest conduction path through the fluid medium between the fluid contact surface and that part of the tissue treatment electrode which is furthest from the fluid contact surface, to (ii) a diameter of the exposed surface portion of the return electrode, is at most 4.5 to 1.

18. An electrosurgical instrument for the treatment of tissue in the presence of an electrically-conductive fluid medium, the instrument comprising
  a semi-flexible instrument shaft capable of being used to exert firm pressure against tissue being treated by said instrument, and
  an electrode assembly at one end of the shaft, the electrode assembly comprising
    a tissue treatment electrode,
    a return electrode, and
    an insulation member electrically insulating the return electrode from the tissue treatment electrode,
  the tissue treatment electrode having an exposed end extending laterally through a cut-out provided in the insulation member,
  wherein the return electrode has a distal end portion with a fluid contact surface which overlies the insulation member in the cut-out's region and faces laterally in a first direction, and wherein the insulation member projects laterally outwardly between said distal end portion and the tissue treatment electrode,
  the tissue treatment electrode facing laterally in a second direction opposite to said first direction, and wherein the treatment electrode and the return electrode are configured in an immovable relationship to one another and the instrument shaft.

19. An electrosurgical instrument as claimed in claim 18, wherein the tissue treatment electrode's dimensions and configurations, the fluid contact surface and the insulation member are such that, when the electrode assembly is immersed in a conductive fluid medium, a ratio of (i) a length of a shortest conduction path through the fluid medium between the fluid contact surface and that part of the tissue treatment electrode which is furthest from the fluid contact surface, to (ii) a length of a shortest conduction path through the fluid medium between the fluid contact surface and the tissue treatment electrode is at most 2 to 1.

20. An electrosurgical instrument as claimed in claim 19, wherein the laterally-projecting portion of the insulation member defines an insulation barrier to divert electrical current flow through the fluid medium thereby to increase said shortest conduction path length between the fluid contact surface and the tissue treatment electrode.

21. An electrosurgical instrument as claimed in claim 20, wherein the first direction defines a treatment axis and said two shortest conduction paths lie in a common plane containing the treatment axis.

22. An electrosurgical instrument as claimed in claim 2, wherein, in at least one transverse plane extending in the first direction, the tissue treatment electrode projects beyond the insulation member in the first direction by a distance which is at least one half of the transverse width of the projecting part of the tissue treatment electrode.

23. An electrode unit for an electrosurgical instrument for the treatment of tissue in the presence of an electrically-conductive fluid medium, the electrode unit comprising
  a semi-flexible shaft having at one end means for connection to an instrument handpiece,
  and, mounted on the other end of the shaft,
  an electrode assembly comprising
    a tissue treatment electrode,
    a return electrode, and
    an insulation member electrically insulating the return electrode from the tissue treatment electrode,
  the tissue treatment electrode having an exposed end extending laterally through a cut-out provided in the insulation member, and
  the return electrode having a fluid contact surface which overlies the insulation member in the cut-out's region, said fluid contact surface being spaced from the tissue treatment electrode in such a manner as to define, in use, a conductive fluid path that completes an electrical circuit between the tissue treatment electrode and the return electrode, and
  wherein the treatment electrode and the return electrode are configured in an immovable relationship to one another and the shaft, the shaft being capable of being used to exert firm pressure against tissue being treated by the instrument.

24. An electrode unit for an electrosurgical instrument for the treatment of tissue in the presence of an electrically-conductive fluid medium, the electrode unit comprising a semi-flexible metal shaft capable of being used to exert firm pressure against tissue being treated by the instrument, said shaft having at one end means for connection to an instrument handpiece, and, mounted at the other end, an electrode assembly comprising
a tissue treatment electrode,
a return electrode, and
an insulation member electrically insulation the return electrode from the tissue treatment electrode,
the tissue treatment electrode having an exposed end extending laterally through a cut-out provided in the insulation member,
wherein the return electrode has a distal end portion with a fluid contact surface which overlies the insulation member the cut-out's region and faces laterally in a first direction, and wherein the insulation member projects laterally outwardly between said distal end portion and the tissue treatment electrode, the tissue treatment electrode facing laterally in a second direction opposite to said first direction,
and wherein the treatment electrode and the return electrode are configured in an immovable relationship to one another and the shaft.

25. Electrosurgical apparatus comprising a radio frequency generator and an electrosurgical instrument for the treatment of tissue in the presence of an electrically-conductive fluid medium, the instrument comprising
a semi-flexible instrument shaft, and
an electrode assembly at one end of the shaft, the electrode assembly comprising
a tissue treatment electrode,
a return electrode, and
an insulation member electrically insulating the return electrode from the tissue treatment electrode,
the tissue treatment electrode having an exposed end extending laterally through a cut-out provided in the insulation member at the distal end portion of the instrument,
the return electrode having a fluid contact surface which overlies the insulation member in the cut-out's region, and
the radio frequency generator having a bipolar output connected to the electrodes,
said fluid contact surface being spaced form the tissue treatment electrode in such a manner as to define, in use, a conductive fluid path that completes an electrical circuit between the tissue treatment electrode and the return electrode
the semi-flexible shaft allowing firm pressure to be exerted against tissue being treated by the instrument, the treatment electrode and the return electrode being configured in an immovable relationship to one another and the shaft.

26. Electrosurgical apparatus comprising a radio frequency generator and an electrosurgical instrument for the treatment of tissue in the presence of an electrically-conductive fluid medium, the instrument comprising a semi-flexible instrument shaft capably of being used to exert firm pressure against tissue being treated by the instrument, and an electrode assembly at one end of the shaft, the electrode assembly comprising
a tissue treatment electrode,
a return electrode, and
an insulation member electrically insulating the return electrode from the tissue treatment electrode, the tissue treatment electrode having an exposed end extending laterally through a cut-out provided in the insulation member,
wherein the return electrode has a distal end portion with a fluid contact surface which overlies the insulation member in the cut-out's region and faces laterally in a first direction, and wherein the insulation member projects laterally outwardly between said distal end portion and the tissue treatment electrode, the tissue treatment electrode facing laterally in a second direction opposite to said first direction,
and wherein the treatment electrode and the return electrode are configured in an immovable relationship to one another and the instrument shaft.

27. Apparatus as claimed in claim 25, wherein the radio frequency generator includes a controller for varying output power delivered to the electrodes.

28. Apparatus as claimed in claim 27, wherein the controller provides output power in first and second output ranges, the first output range being for powering the electrosurgical instrument for tissue desiccation, and the second output range being for powering the electrosurgical instrument for tissue removal by cutting or vaporisation, and
wherein a load impedance presented to the generator in the second output range is at least ten times the load impedance presented to the generator in the first output range.

29. Apparatus as claimed in claim 28, wherein the first output range is from about 140 volts to 200 volts, and the second output range is from about 250 volts to 600 volts, the voltages being peak voltages.

30. Apparatus as claimed in claim 28, wherein the controller alternates the output power between first and second powers in the first and second output ranges.

31. Apparatus as claimed in claim 28, wherein the controller pulses the output power at a power within the second output range.

32. An electrosurgical method using an electrosurgical apparatus having at least a tissue desiccation mode and a tissue vaporisation mode, the apparatus having a radio frequency generator coupled to an electrode assembly for the treatment of tissue in the presence of an electrically-conductive fluid medium, the electrode assembly comprising a tissue treatment electrode, a return electrode, and an insulation member electrically insulating the return electrode from the tissue treatment electrode, the tissue treatment electrode having an exposed end extending laterally through a cut-out provided in the insulation member at distal end of the assembly, and the return electrode having a fluid contact surface spaced from the exposed end of the tissue treatment electrode by the insulation member, the treatment electrode and the return electrode being configured in an immovable relationship to one another; the method comprising the steps of:
introducing the electrode assembly into a selected operation site with the issue treatment electrode adjacent to the tissue to be treated;
immersing the fluid contact surface of the return electrode and the exposed end of the tissue treatment electrode in electrically-conductive fluid; and
controlling the output power of the radio frequency generator to lie within a first output range for the tissue desiccation mode and to lie within a second range for the tissue vaporisation mode, the first output range being such that the power supplied to the electrode assembly maintains the conductive fluid adjacent to the tissue treatment electrode substantially at boiling point for tissue desiccation without creating a vapour pocket surrounding the tissue treatment electrode, and the second output range is such that the output power supplied to the electrode assembly for vaporisation of tissue is such as to maintain a vapour pocket surrounding the tissue treatment electrode.

33. A method as claimed in claim 32, wherein the first output range is from about 150 volts to 200 volts and the second output range is from about 250 volts to 600 volts, the voltages being peak voltages.

34. A method as claimed in claim 32, wherein the electrode assembly is introduced into the selected operation site in a direction which is generally along the surface of the tissue to be treated, and with the tissue treatment electrode facing the tissue to be treated.

35. An electrosurgical instrument for the treatment of tissue in the presence of an electrically-conductive fluid medium, the instrument comprising:

- a semi-flexible instrument shaft capable of being used to exert firm pressure against tissue being treated by said instrument,
- a suction pump for removing vapour bubbles via the instrument shaft's interior, and
- an electrode assembly at one end of the shaft, the electrode assembly comprising
  - a tissue treatment electrode,
  - a return electrode, and
  - an insulation member electrically insulating the return electrode from the tissue treatment electrode, the tissue treatment electrode having an exposed end extending laterally through a cut-out provided in the insulation member at a distal end portion of the instrument, and the return electrode having a fluid contact surface which overlies the insulation member in the region of the cut-out, said fluid contact surface being spaced from the tissue treatment electrode in such a manner as to define, in use, a conductive fluid path that completes an electrical circuit between the tissue treatment electrode and the return electrode, and wherein the treatment electrode and the return electrode are configured in an immovable relationship to one another and the instrument shaft.

\* \* \* \* \*